United States Patent [19]

Bentley

[11] Patent Number: 4,461,914

[45] Date of Patent: Jul. 24, 1984

[54] METHOD FOR THE PREPARATION OF 1-(4'-AMINO-3',5'-DICHLOROPHENYL)-2-ALKYL(OR DIALKYL)AMINOETHANOLS

[75] Inventor: Terence J. Bentley, East Windsor, N.J.

[73] Assignee: American Cyanamid Company, Stamford, Conn.

[21] Appl. No.: 462,856

[22] Filed: Feb. 1, 1983

[51] Int. Cl.$^3$ .............................................. C07C 85/24
[52] U.S. Cl. ...................................... 564/357; 564/358
[58] Field of Search ................................ 564/358, 357

[56] References Cited

U.S. PATENT DOCUMENTS

| | | | |
|---|---|---|---|
| 1,767,423 | 6/1930 | Adams | 564/358 X |
| 2,308,232 | 1/1943 | Scheuing et al. | 564/357 |
| 3,139,441 | 6/1964 | Biel | 564/357 X |
| 3,448,153 | 6/1969 | Cavitt et al. | 564/357 X |
| 3,657,244 | 4/1972 | Mentrup et al. | 564/357 X |
| 3,937,838 | 2/1976 | Wetterlin et al. | 564/357 X |
| 4,273,939 | 6/1981 | Barnett et al. | 564/358 |
| 4,307,248 | 12/1981 | Barnett et al. | 564/358 |

*Primary Examiner*—Paul F. Shaver
*Attorney, Agent, or Firm*—Estelle J. Tsevdos; Alphonse R. Noë

[57] ABSTRACT

A method for the preparation of 1-(4'-amino-3',5'-dichlorophenyl)-2-alkyl)or dialkyl)aminoethanols. The method involves preparation of the above compounds from the corresponding aminoketones by reduction with hydrogen in the presence of platinum oxide catalyst and a promoter, such as stannous chloride.

5 Claims, No Drawings

METHOD FOR THE PREPARATION OF 1-(4'-AMINO-3',5'-DICHLOROPHENYL)-2-ALKYL(OR DIALKYL)AMINOETHANOLS

The invention herein described relates to a method for the preparation of certain biologically active 1-(4'-amino-3',5'-dichlorophenyl)-2-alkyl(or dialkyl)aminoethanol compounds. These compounds are particularly effective as promotors of animal growth and for improving the lean meat to fat ratio in domestic and farm animals. The method of the invention involves preparation of the subject compounds from the corresponding aminoketones by reduction with hydrogen in the presence of platinum oxide catalyst and a suitable promotor. Stannous chloride is a particularly useful promotor.

By way of background, compounds related to the compounds of the subject invention are disclosed in U.S. Pat. No. 3,536,712. The patentees disclose methods for the synthesis of said compounds and state that these compounds are useful for enhancing blood circulation, and as bronchodilators, analgesics, sedatives, antipyretics, antiphlogistics and antitussives in warm-blooded animals. Other related 1-aminodihalophenyl-2-aminoethanols and their derivatives are disclosed in Japanese Kokai No. 77 83,619 (Chemical Abstracts 87, 201061r), German Offenlegungsschrift No. 2,804,625 (1979), German Offenlegungsschrift No. 2,157,040 (1973), German Offenlegungsschrift No. 2,261,914 (1974), European Patent Application No. 8,715 (1980), and Netherlands Patent Application No. 7,303,612 (1973). These applications disclose uses of these compounds as analgesics; broncholytic, antiinflammatory, uterine spasmolytic, β-mimetic and/or β-blocking activities; antispasmolytic activity on cross-striped muscle structure; for reducing blood pressure by peripheral vasodilation; for treating allergies; and for tocology.

European Patent Application No. 26,298 (1979), discloses the use of such compounds for animal growth promotion and for increasing lean meat desposition and/or improving the lean meat to fat ratio in domestic and farm animals.

U.S. Pat. No. 3,536,712 discloses the reduction of an analogous aminoketone (III) with a complex metal hydride to the corresponding aminoalcohol as shown below:

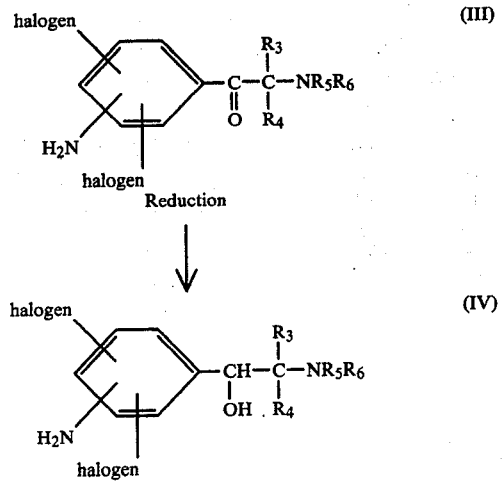

wherein in the above reaction sequence, the word "halogen" stands for bromine, chlorine, fluorine and iodine; while $R_3$ to $R_6$ are hydrogen or some other suitable substituent. U.S. Pat. No. 4,119,710 refers to the catalytic reduction of aminoketones with hydrogen and a catalyst.

More specifically the present invention involves a method for the preparation of biologically active compounds of structural formula:

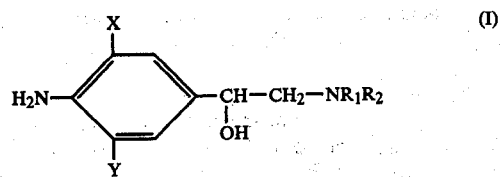

wherein $R_1$ and $R_2$ are hydrogen or $C_1$–$C_4$ alkyl; X and Y are hydrogen, bromine, chlorine or fluorine; and pharmaceutically acceptable salts thereof; from aminoketone of formula (II)

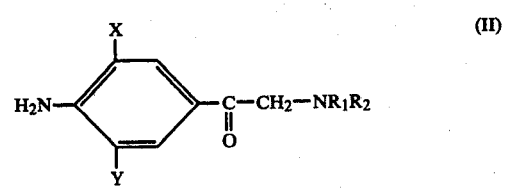

wherein $R_1$, $R_2$, and X and Y are as defined above. The invention utilizes a catalytic hydrogenation procedure.

It has been observed that when reduction was attempted with a formula (II) aminoketone under a variety of conditions (c.f., U.S. Pat. No. 4,119,710 wherein catalytic reduction of aminoketones with hydrogen is disclosed) to obtain the desired aminoalcohols of formula (I), the recovered material was mainly unchanged aminoketone (formula II) mixed with small amounts of the desired material.

In light of the foregoing summary of some demands and limitations of conventional methods for the production of 1-(4'-amino-3',5'-dichlorophenyl)-2-alkyl(or dialkyl)aminoethanols, an improved method for the preparation of these biologically active animal-growth-regulating compounds is highly desirable. Accordingly, an object of this invention is to provide a new and useful method for producing 1-(4'-amino-3',5'-dichlorophenyl)-2-alkyl(or dialkyl)aminoethanol compounds. This object is manifest in the following description and particularly delineated in the appended claims.

The compounds of structural formula:

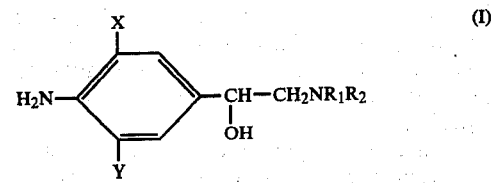

wherein $R_1$, $R_2$, X and Y are hereinabove defined, are biologically active and are especially suitable for animal growth promotion and for improving the lean meat to fat ratio in domestic and farm animals. Among the compounds of formula (I), the compound of formula (Ia)

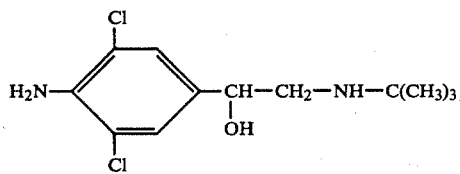

is of particular interest as an animal growth regulant and for improving the lean meat to fat ratio in said animals.

In general, the compounds of structural formula (I) can be prepared from the corresponding aminoketone compounds of structural formula (II) by reduction with a complex metal hydride. This reaction is illustrated as follows:

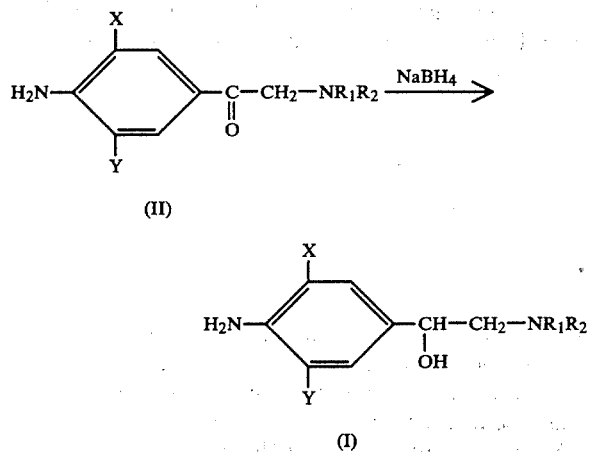

wherein $R_1$, $R_2$, X and Y are as above defined.

It has been unexpectedly found that an aminoketone of structural formula (II) may be reduced under mild reaction conditions in a satisfactory manner with hydrogen and platinum oxide catalyst in the presence of a promoter selected from the group consisting of: stannous chloride, ferrous and ferric chloride, cobaltous chloride and cerous chloride (preferably stannous chloride); and a solvent selected from: methyl alcohol, ethyl alcohol, propyl alcohol, isopropyl alcohol, and mixtures thereof; at a temperature range of about 10° to 30° C.; under a hydrogen atmosphere at a pressure of about 1.69 to 4.92 kg cm$^{-2}$ (24–70 psig) [preferably 2.1 to 2.8 kg cm$^{-2}$ (30–40 psig)]; for a period of time sufficient to essentially complete the reaction. The thus obtained aminoalcohols of formula (I) may be isolated from the reaction mixture and further purified by standard laboratory procedures.

The compounds of structural formula (I), especially the compound of structural formula (Ia), are useful animal growth regulants and effective for increasing lean meat deposition and/or improving the lean meat to fat ratio in poultry, swine, sheep, goats, domestic pets and cattle.

Animal feed compositions effective as animal growth regulants and effective for increasing lean meat deposition and/or increasing lean meat to fat ratio are generally prepared by admixing a formula (I) aminoalcohol or acid addition salt thereof, or an animal feed supplement containing said compound, with a sufficient amount of animal feed to provide from about 1 to 1000 ppm of said compound in feed.

Animal feed supplements can be prepared by admixing on a weight basis about 70 to 95% of a formula (I) aminoalcohol, or an acid addition salt thereof, with about 5 to 20% of a suitable carrier or diluent selected from the group consisting of: alfalfa meal; soybean meal; cottonseed oil meal; linseed oil meal; sodium chloride; cornmeal; cane molasses; urea; bone meal; and corncob meal and the like; and mixtures thereof.

The preferred medicated swine, cattle, sheep and goat feeds generally contain from 0.01 to 400 g of active ingredient per ton of feed; the optimum amount for these animals usually is about 50 to 300 g per ton of feed.

The preferred poultry and domestic pet feeds usually contain from about 0.01 to 400 g (preferably 10 to 400 g) of active ingredient per ton of feed.

The invention is further illustrated by the non-limiting Examples set forth below.

EXAMPLE 1

Preparation of 1-(4'-amino-3',5'-dichlorophenyl)-2-t-butylamino ethanol from the corresponding ketone by catalytic hydrogenation in the presence of a mixed platinum oxide/stannous chloride catalyst A mixture of 2-t-butylamino-4'-amino-3',5'-dichloroacetophenone hydrochloride (1.0 g), stannous chloride (0.05 g), platinum oxide (0.25 g) and ethanol (25 ml) is agitated (shaken) vigorously at room temperature in a hydrogen atmosphere under an initial pressure of 4.78 kg cm$^{-2}$ (68 psig). In about 16 hours, the uptake of hydrogen appears to be complete. Thin layer chromatography (silica gel; eluent: 0.5% aq.NH$_3$/5% MeOH/CH$_2$Cl$_2$) indicates the absence of starting material. The catalyst is filtered off. The filtrate is evaporated to dryness under vacuum. The residue is dissolved in water. The solution made alkaline with 10% sodium hydroxide, and is then extracted with methylene chloride (3×25 ml). The extracts are combined, dried over sodium sulfate, and evaporated to dryness under vacuum. There is obtained 0.65 g (69.8% yield) of title product with satisfactory mass and infrared spectra. The spectra indicate that during the reaction no ring dehalogenation took place.

EXAMPLE 2

Attempted preparation of 1-(4'-amino-3',5'-dichlorophenyl)-2-t-butylaminoethanol from the corresponding ketone via catalytic hydrogenation using Raney Nickel catalyst A mixture of 2-t-butylamino-4'-amino-3',5'-dichloroacetophenone hydrochloride (1.0 g), Raney nickel catalyst (1.0 g), and methanol (25 ml) is agitated (shaken) vigorously at room temperature in a hydrogen atmosphere maintained under a pressure of 1.9 kg cm$^{-2}$ (27 psig) for a period of 3 hours. During this time little or no hydrogen uptake is noted.

Additional Raney nickel catalyst (1.0 g) is introduced into the reaction mixture. The mixture is agitated at room temperature in a hydrogen atmosphere at a pressure of 1.9 kg cm$^{-2}$ (27 psig) for an additional 20 hours. Thin layer chromatography (silica gel; eluent: 0.5% aq.NH$_3$/5% MeOH/CH$_2$Cl$_2$) and mass spectra indicate the presence of approximately 10% title product and 90% starting material.

EXAMPLE 3

Attempted preparation of 1-(4'-amino-3',5'-dichlorophenyl)-2-t-butylaminoethanol from the corresponding ketone via hydrogenation in the presence of Palladium catalyst A mixture of 2-t-butylamino-4'-amino-3',5'-dichloroacetophenone hydrochloride (1.0 g), palladium catalyst (0.5 g; 5% Pd on carbon support), and methanol (20 ml) is agitated (shaken) vigorously at room temperature in a hydrogen atmosphere maintained under a pressure of about 2.4 to 2.6 kg cm$^{-2}$ (34-37 psig) for a period of about 3 hours. The catalyst is removed by filtration. The solvent is then evaporated under vacuum. Analysis of the solid residue by thin layer chromatography (silica gel; eluent: 0.5% aq.NH$_3$/5% MeOH/CH$_2$Cl$_2$) indicates the presence of about 10% title product, about 40% of 1-(4'-aminophenyl)-2-t-butylaminoethanol, and 50% of starting material.

EXAMPLE 4

Attempted preparation of 1-(4'-amino-3',5'-dichlorophenyl)-2-t-butylaminoethanol from the corresponding ketone via hydrogenation in the presence of Platinum catalyst A mixture of 2-t-butylamino-4'-amino-3',5'-dichloroacetophenone hydrochloride (1.0 g), platinum catalyst (0.1 g; 5% Pt on carbon support), and methanol (20 ml) is agitated (shaken) vigorously at room temperature in a hydrogen atmosphere under a pressure of about 3.5 kg cm$^{-2}$ (50 psig) for about 5 hours and 40 minutes. During this time little or no hydrogen uptake is noted. Additional platinum catalyst (0.25 g; 5% Pt. on carbon support) is introduced into the reaction mixture. Hydrogenation is continued at room temperature for 18 hours under a pressure of 2.3-2.7 kg cm$^{-2}$ (32.5-38 psig). Thin layer chromatography (as in Examples 1-3) indicates that there is very little or no reduction. Concentrated hydrochloric acid (10 drops) is added. Hydrogenation is continued under a pressure of 2.8 kg cm$^{-2}$ (40 psig) for an additional 18 hours. Thin layer chromatography indicates a mixture of about 10% title product and about 90% starting material.

EXAMPLE 5

Attempted preparation of 1-(4'-amino-3',5'-dichlorophenyl)-2-t-butylaminoethanol from the corresponding ketone via catalytic hydrogenation in the presence of platinum oxide catalyst A mixture of 2-t-butylamino-4'-amino-3',5'-dichloroacetophenone hydrochloride (1.0 g), platinum oxide (0.25 g), and methanol (25 ml) is agitated (shaken) vigorously at room temperature in a hydrogen atmosphere under a pressure of about 2.8-3.5 kg cm$^{-2}$ (40-50 psig). The reaction is monitored by thin layer chromatography (TLC). After 50 minutes of reaction time, only starting material is present. Concentrated hydrochloric acid (10 drops) is added. Hydrogenation is continued for an additional 5 hours. After 5 hours, TLC indicates starting material and about 5% of title compound to be present.

EXAMPLE 6

By the method described in Example 1, the following products are prepared by reducing their corresponding ketone precursors:

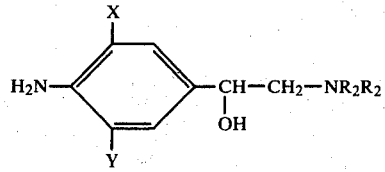

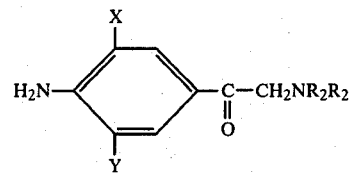

| R$_1$ | R$_2$ | Product MP °C. |
|---|---|---|
| H | i-C$_3$H$_7$ | 92-93 |
| i-C$_3$H$_7$ | i-C$_3$H$_7$ | 159-162 (hydrochloride salt) |
| H | n-C$_4$H$_9$ | 95-98 |
| H | i-C$_4$H$_9$ | |
| H | C$_2$H$_5$ | |
| H | n-C$_3$H$_7$ | |
| H | CH$_3$ | 168-170 dec. (hydrochloride salt) |

What is claimed is:

1. A method for the preparation of a compound of structural formula, wherein R$_1$ and R$_2$ are hydrogen or C$_1$-C$_4$ alkyl; X and Y are hydrogen, bromine, chlorine or fluorine; or pharmaceutically-acceptable acid addition salts thereof, said method comprising: reducing a compound of structural formula, wherein R$_1$, R$_2$, X and Y are as hereinabove defined, by reacting same with hydrogen in the presence of platinum oxide catalyst and a promoter selected from the group consisting of stannous chloride, ferrous chloride, ferric chloride, cobaltous chloride or cerous chloride; and a solvent selected from the group consisting of methyl alcohol, ethyl alcohol, propyl alcohol, isopropyl alcohol, or mixtures thereof; at a temperature range of about 10° C. to 30° C.; and at a pressure of about 1.69 kg cm$^{-2}$ to 4.92 kg cm$^{-2}$; for a period of time sufficient to essentially complete the reaction.

2. A method according to claim 1, wherein the promoter is stannous chloride.

3. A method according to claim 2, wherein X and Y are chlorine; R$_1$ is hydrogen and R$_2$ is C$_1$-C$_4$ alkyl.

4. A method according to claim 3, wherein R$_2$ is t-butyl; the solvent is ethyl alcohol and the pressure is 4.0 kg cm$^{-2}$.

5. A method according to claim 1, wherein the pressure is 2.1 to 2.8 kg cm$^{-2}$.

* * * * *